United States Patent
Nishida et al.

(10) Patent No.: US 10,514,536 B2
(45) Date of Patent: Dec. 24, 2019

(54) OBSERVATION OPTICAL SYSTEM

(71) Applicant: Konica Minolta, Inc., Tokyo (JP)

(72) Inventors: Maiko Nishida, Tokyo (JP); Naoki Hirose, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 150 days.

(21) Appl. No.: 15/617,664

(22) Filed: Jun. 8, 2017

(65) Prior Publication Data
US 2017/0357085 A1 Dec. 14, 2017

(30) Foreign Application Priority Data

Jun. 8, 2016 (JP) ................. 2016-114830

(51) Int. Cl.
*G02B 25/00* (2006.01)
*G02B 13/18* (2006.01)
*G02B 13/00* (2006.01)
*G02B 21/02* (2006.01)
*A61B 90/00* (2016.01)

(52) U.S. Cl.
CPC ....... *G02B 25/007* (2013.01); *G02B 13/0065* (2013.01); *G02B 13/18* (2013.01); *G02B 21/02* (2013.01); *G02B 25/001* (2013.01); *G02B 25/008* (2013.01); *A61B 90/361* (2016.02); *A61B 2090/3616* (2016.02)

(58) Field of Classification Search
CPC .... G02B 21/02; G02B 25/001; G02B 25/007; G02B 25/008; G02B 13/0065
USPC ................. 359/643, 656, 657, 658
See application file for complete search history.

(56) References Cited

U.S. PATENT DOCUMENTS 5,191,470 A * 3/1993 Wickholm ............. G02B 21/20
                                                                359/375
5,499,140 A * 3/1996 Betensky ............... G02B 15/14
                                                                359/407
5,850,311 A * 12/1998 Hankawa ............. G02B 25/001
                                                                359/644

(Continued)

FOREIGN PATENT DOCUMENTS

| JP | H09-218358 A | 8/1997 |
|---|---|---|
| JP | H11-194400 A | 7/1999 |
| JP | 2011-513800 A | 4/2011 |

OTHER PUBLICATIONS

"Geometrical Optics." Introduction to Optics, by Frank L. Pedrotti et al., Pearson Prentice-Hall, 2007, pp. 16-49.*

(Continued)

*Primary Examiner* — Zachary W Wilkes
(74) *Attorney, Agent, or Firm* — Osha Liang LLP

(57) ABSTRACT

An observation optical system of a real-image type includes, in order from the object side, an objective system, a reverse-erecting system that erects an inverted image formed by the objective system, and an eyepiece system that allows a pupil to observe an erect image formed by the reverse-erecting system. The objective system includes, in order from the object side, a first lens having a negative power and a second lens having a positive power. The eyepiece system includes, in the order from the object side, a third lens having a positive power, a fourth lens having a negative power, a fifth lens having a positive power, and a sixth lens having a positive power.

4 Claims, 3 Drawing Sheets

(56) References Cited

U.S. PATENT DOCUMENTS

| | | | | |
|---|---|---|---|---|
| 6,046,853 A * | 4/2000 | Yano | ............... | G02B 27/646 |
| | | | | 359/407 |
| 6,166,861 A * | 12/2000 | Koizumi | ............ | G02B 9/12 |
| | | | | 359/644 |
| 9,869,850 B2 * | 1/2018 | Jin | ................. | G02B 25/001 |
| 2015/0362720 A1 * | 12/2015 | Saito | .............. | G02B 25/001 |
| | | | | 359/644 |
| 2016/0313570 A1 * | 10/2016 | Arai | ................. | G02B 13/02 |
| 2017/0075128 A1 * | 3/2017 | Tanami | .......... | G02B 27/646 |

OTHER PUBLICATIONS

Song, Seok. "Chapter 1. Ray Optics." 2018.*
"Len Shape."; "Aberration Balancing" Melles Griot Practical Application of Light: Catalogue, 1999, pp. 1.17, 1.27-1.28.*
Notification of Reasons for Refusal issued in Japanese Patent Application No. 2016-114830, dated Nov. 5, 2019 (6 pages).

* cited by examiner

SPHERICAL
ABERRATION (Dpt)

ASTIGMATISM (Dpt)

DISTORTION
ABERRATION (%)

OBSERVATION OPTICAL SYSTEM

This application claims a priority under the Paris Convention of Japanese patent application No. 2016-114830 filed on Jun. 8, 2016, the entirety of which is incorporated herein by references.

TECHNICAL FIELD

The present invention relates to an observation optical system used for loupes for medical care, manual work, and the like.

BACKGROUND

As loupes for medical care, manual work, and the like, there are used spectacle-type loupes to be worn like a pair of glasses, or head-mounting type loupes to be fixed to the head, which allow manual work to be performed with both hands. Such a loupe is expected to be reduced in size and weight to reduce the burden of mounting, with various aberrations corrected from the center to the periphery of the loupe view so as not to disturb manual work.

Patent Literature 1 discloses an observation system for use as binoculars or the like, the observation system including an eyepiece lens that provides a wide angle of view while downsizing the entire system. However, the optical system of Patent Literature 1 is configured to have positive and negative objective lenses, and therefore reducing the size and weight for ease of wearing results in insufficient correction of aberration and fails to ensure good performance.

CITATION LIST

Patent Literature

Patent Literature 1 Japanese Patent Laid-Open No. 09-218358

SUMMARY

One or more embodiments of the present invention provide a small-size and light-weight observation optical system with favorably-corrected aberration.

In one or more embodiments of the present invention, an observation optical system of a real-image type comprises, in an order from an object side, an objective system, a reverse-erecting system configured to erect an inverted image formed by the objective system, and an eyepiece system configured to allow a pupil to observe an erect image formed by the reverse-erecting system, in which the objective system may consist essentially of, in an order from the object side, a first lens having a negative power and a second lens having a positive power, and the eyepiece system may consist essentially of, in an order from the object side, a third lens having a positive power, a fourth lens having a negative power, a fifth lens having a positive power, and a sixth lens having a positive power.

DETAILED DESCRIPTION

Hereinafter, an observation optical system 10 which may represent one or more embodiments of the present invention will be described, referring to FIG. 1A. Note that the observation optical system 10 illustrated in FIG. 1A has the same configuration as that of an observation optical system 10A of an Example 1 described below.

Figure 1A:
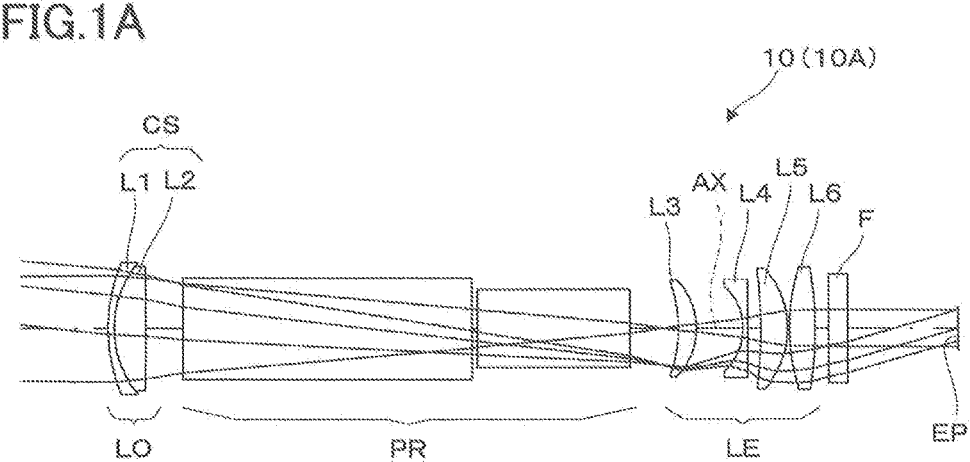
FIG. 1A is a cross-sectional view illustrating an observation optical system of the present embodiment and an Example 1.

As illustrated in FIG. 1A, the observation optical system 10 is a single-focus optical system of a real-image type including, in the order from the object side, an objective system LO, a reverse-erecting system PR, and an eyepiece system LE. The observation optical system 10 is fixed to a lens barrel (not illustrated) or the like, and used for loupes for medical care, manual work, and the like. As such loupes, there are used spectacle-type or head-mounting type loupes so as to allow manual work to be performed with both hands.

In the observation optical system 10, the objective system LO is intended to collect light beams to form a real image. The objective system LO includes, in the order from the object side, a first lens L1 having a negative power and a second lens L2 having a positive power. In the objective system LO, the first lens L1 and the second lens L2 are joined o to form a cemented lens CS. Accordingly, magnification chromatic aberration may be favorably-corrected. The cemented lens CS has a positive power as a whole. The first and second lenses L1 and L2 are made of glass.

The reverse-erecting system PR is intended to erect an inverted image formed by the objective system LO. As the reverse-erecting system PR prisms are used, for example. In the example of FIG. 1A, the reverse-erecting system PR includes two glass prisms. Note that, although the image on a pupil EP of the observation optical system 10 is described to be inverted in the illustrated example for a convenience of the explanation, the top and bottom and the right and left are actually reversed due to the effect of the reverse-erecting system PR so that the image at the pupil EP is observed to be erect.

The eyepiece system LE is intended to allow a human eye to observe, via the pupil EP, the erect image formed by the reverse-erecting system PR. The eyepiece system LE includes, in the order from the object side, a third lens L3 having a positive power, a fourth lens L4 having a negative power, a fifth lens L5 having a positive power, and a sixth lens L6 having a positive power. The eyepiece system LE has a positive power as a whole. In the eyepiece system LE, the third lens L3 has a concave surface at the object side. As the observation optical system 10 is reduced in size, it is required to increase the power of the objective system LO and the power of the eyepiece system LE, whereby high-order aberration is likely to occur due to a strong refraction effect. It is therefore possible to prevent the incidence angle of light beams from becoming too large around the lens surface and suppress occurrence of a high-order aberration by rendering the object side surface of the third lens L3 into a concave surface. In addition, the fourth lens L4 has a concave surface at the object side. Accordingly, distortion aberration that occurs on the third lens L3 can be corrected.

Note that the eyepiece system LE may have a lens at least one side of which is aspherical. That is, at least one surface of the lenses L3-L6 may be aspherical. Accordingly, off-axis aberration such as field curvature or image surface curvature as well as on-axis aberration can be favorably-corrected. For example, in observation optical systems 10B and 10C of examples 2 and 3 described below, lens surfaces of the object side and the pupil EP side of the sixth lens L6 which is closest to the pupil EP side are rendered aspherical (see FIGS. 2A and 3A). The third to sixth lenses L3 to L6 are made of glass.

In the observation optical system 10, a parallel flat plate F is provided between the eyepiece system LE and the pupil EP. The parallel flat plate F may be a lens for diopter adjustment when the observation optical system 10 is of a spectacle type. Note that, when the observation optical system 10 is used for an application that requires wavelength selection, the parallel flat plate F may be subjected to coating for the wavelength selection.

The observation optical system 10 described above may essentially or substantially consist of the objective system LO, the reverse-erecting system PR, and the eyepiece system LE. The observation optical system 10 of such a real-image type has a shorter focus distance and can have a smaller diameter of the objective system LO than the observation optical system of a virtual-image type. Here, it is necessary to increase the power of the objective system LO and the power of the eyepiece system LE in order to reduce the total length and the size in the radial direction of the observation optical system 10. A configuration providing the objective system LO with a negative lens and a positive lens from the object side can increase the power of the objective system LO while suppressing the thickness of the outer periphery of the lenses, and suppress occurrence of spherical aberration after having executed thinning for weight reduction. In addition, providing a positive lens as the third lens L3 located closest to the object side in the eyepiece system LE can reduce the size of the eyepiece system LE, whereby spherical aberration that occurs in the objective system LO and the third lens L3 can be corrected by the fourth lens L4 having a negative power. In addition, providing positive lenses as two lenses located closest to the pupil EP side can correct the field curvature or image surface curvature and astigmatism.

EXAMPLE

Hereinafter, there is described an example of the observation optical system according to the present invention. The symbols used in respective examples are as follows.
R: paraxial curvature radius
D: on-axis surface interval
n: refractive index for d-line of lens material
vd: Abbe number of lens material In addition, the symbol Surf.N denotes the surface number, the symbol INF denotes infinity or ∞, and the symbol EP denotes the pupil side.

In respective examples, surfaces bearing a symbol "★" after the respective surface numbers are aspherical surfaces, and the shape of an aspherical surface is expressed by the following "formula 1" with the apex of the surface being the origin, the Z axis taken in the optical axis direction, and "h" denoting the height in a direction perpendicular to the optical axis AX.

$$Z = \frac{h^2/R}{1 + \sqrt{1 - (1+K)h^2/R^2}} + \sum A_i h^i \quad \text{(fomula 1)}$$

where
$A_i$: i-th order aspherical coefficient or factor
R: curvature radius
K: conic constant Example 1

Optical data of the observation optical system of Example 1 are listed below. Here, the visual field range is a range which may be observed on the object surface when looking into the observation optical system from the pupil side.
magnification: 3.3 (times)
diopter: −1.0 (Dpt)
object distance: 402.2 (mm)
visual field range: φ85 (mm)

Data of the lens surface or the like of the observation optical system of Example 1 are listed below in table 1.

TABLE 1

| Surf. N | R (mm) | D (mm) | n | vd |
|---|---|---|---|---|
| 1 | 18.309 | 0.64 | 1.90366 | 31.32 |
| 2 | 11.109 | 3.34 | 1.65844 | 50.85 |
| 3 | −311.772 | 3.9 | | |
| 4 | INF | 30.57 | 1.75520 | 27.53 |
| 5 | INF | 0.52 | | |
| 6 | INF | 16.18 | 1.75520 | 27.53 |
| 7 | INF | 5.1 | | |
| 8 | −14.262 | 1.89 | 1.90366 | 31.32 |
| 9 | −7.38 | 4.93 | | |
| 10 | −6.123 | 0.5 | 1.76182 | 26.61 |
| 11 | −393.742 | 1.39 | | |
| 12 | −46.68 | 2.89 | 1.83481 | 42.72 |
| 13 | −9.59 | 0.2 | | |
| 14 | 21.805 | 2.7 | 1.77250 | 49.62 |
| 15 | −38.325 | 1.43 | | |
| 16 | INF | 2 | 1.51680 | 64.20 |
| 17 | INF | 11.5 | | |
| 18 (EP) | INF | | | |

FIG. 1A is a sectional view of the observation optical system 10A of Example 1. The observation optical system 10A has the objective system LO, the reverse-erecting system PR, and the eyepiece system LE. The objective system LO has the first lens L1 having a negative power and the second lens L2 having a positive power. The lenses L1 and L2 are joined to each other. The eyepiece system LE has the third lens L3 having a positive power and having a concave surface at the object side, the fourth lens L4 having a negative power and having a concave surface at the object side, the fifth lens L5 having a positive power, and the sixth lens L6 having a positive power. As for the lenses, the first lens L1 is located at the object side and the sixth lens L6 is located at the pupil EP side. The first to sixth lenses L1 to L6 are made of glass. Note that, although the symbol F indicates a parallel flat plate, it may be a lens for diopter adjustment when the observation optical system 10A is of a spectacle type. In addition, the symbol EP indicates the designed pupil position (the same goes for the following examples).

Figure 1B:
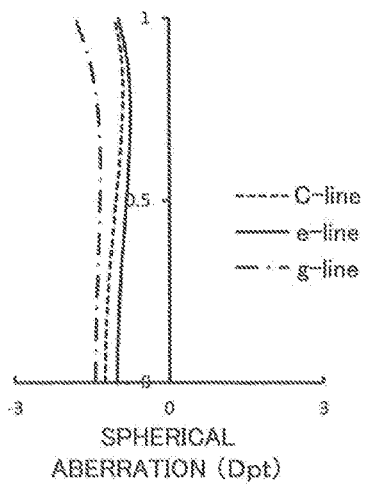
FIGS. 1B to 1D illustrate aberration charts of the observation optical system of FIG. 1A.
Figure 1C:
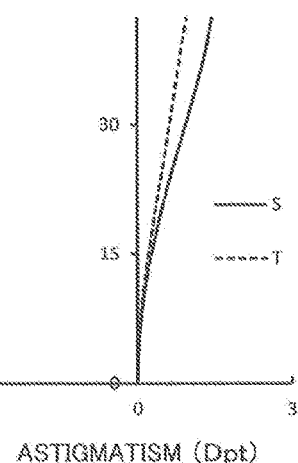
Figure 1D:
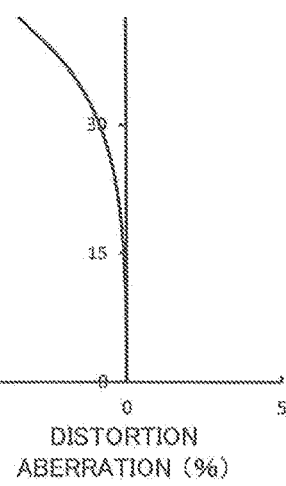

FIGS. 1B to 1D respectively illustrate spherical aberration, astigmatism, and distortion aberration relating to virtual images of the observation optical system of Example 1 illustrated in FIG. 1A. Note that the spherical aberration chart is illustrated with ODpt being a reference and −1 Dpt being a target value. In addition, the astigmatism chart and the distortion aberration chart have −1 Dpt as a reference (the same goes for the following examples).

Example 2

Optical data of the observation optical system of Example 2 are listed below.
magnification: 4.3 (times)
diopter: −1.0 (Dpt)
object distance: 395.6 (mm)
visual field range: φ75 (mm)
Data of the lens surface or the like of the observation optical system of Example 2 are listed below in table 2.

TABLE 2

| Surf. N | R (mm) | D (mm) | n | vd |
| --- | --- | --- | --- | --- |
| 1 | 20.885 | 0.74 | 1.85026 | 32.27 |
| 2 | 12.256 | 3.3 | 1.65844 | 50.85 |
| 3 | −1346.3 | 10.51 | | |
| 4 | INF | 30.57 | 1.75520 | 27.53 |
| 5 | INF | 0.52 | | |
| 6 | INF | 16.18 | 1.75520 | 27.53 |
| 7 | INF | 5.05 | | |
| 8 | −21.339 | 2.25 | 1.90366 | 31.32 |
| 9 | −7.759 | 2.75 | | |
| 10 | −5.619 | 0.5 | 1.72825 | 28.32 |
| 11 | 30.267 | 0.94 | | |
| 12 | 86.2 | 3.9 | 1.77250 | 49.62 |
| 13 | −9.824 | 0.23 | | |
| 14* | 22.874 | 3.5 | 1.62263 | 58.164 |
| 15* | −21.26 | 1.91 | | |
| 16 | INF | 2 | 1.51680 | 64.20 |
| 17 | INF | 11.5 | | |
| 18 (EP) | INF | | | |

Aspherical coefficients of the observation optical system of Example 2 are listed in table 3 below. Note that, from now on (including lens data of the list), values represented by powers of ten (for example, $2.5*10^{-02}$) are expressed using E (for example, 2.5E-02).

TABLE 3

Fourteenth Surface

K = −5.00, A4 = −3.300E−05, A6 = −6.887E−07, A8 = 4.256E−08,
A10 = −2.862E−10

Fifteenth surface

K = 2.46, A4 = −5.112E−05, A6 = 8.161E−07, A8 = 9.092E−09,
A10 = 5.489E−11

Figure 2A:
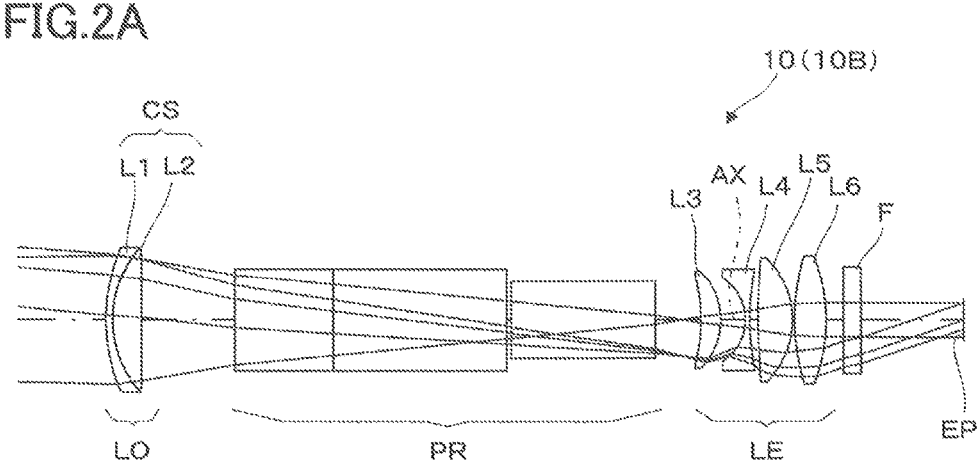
FIG. 2A is a cross-sectional view illustrating an observation optical system of Example 2.

FIG. 2A is a cross-sectional view of the observation optical system 10B of Example 2. The observation optical system 10B has the objective system LO, the reverse-erecting system PR, and the eyepiece system LE. The objective system LO has the first lens L1 having a negative power and the second lens L2 having a positive power. The lenses L1 and L2 are joined to each other. The eyepiece system LE has the third lens L3 having a positive power and having a concave surface at the object side, the fourth lens L4 having a negative power and having a concave surface at the object side, the fifth lens L5 having a positive power, and the sixth lens L6 having a positive power. As for the lenses, the first lens L1 is located at the object side, and the sixth lens L6 is located at the pupil EP side. The first to sixth lenses L1 to L6 are made of glass. The lens surfaces at the object side and the pupil EP side of the sixth lens L6 are aspherical.

Figure 2B:
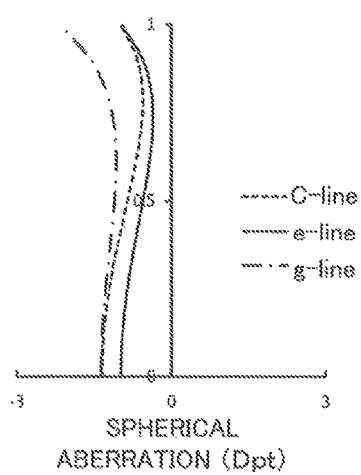
FIGS. 2B to 2D illustrate aberration charts of the observation optical system of FIG. 2A.
Figure 2C:
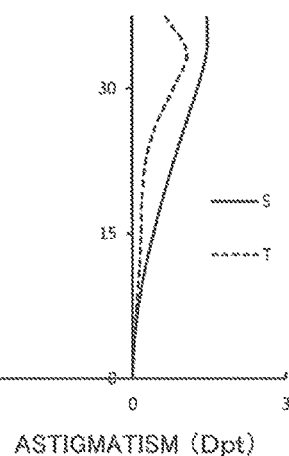
Figure 2D:
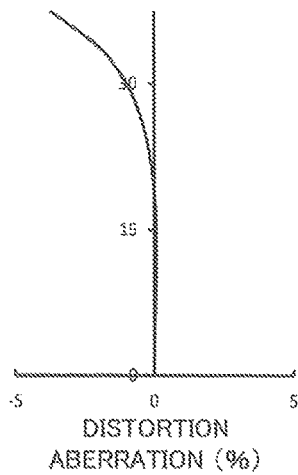

FIGS. 2B to 2D respectively illustrate spherical aberration, astigmatism, and distortion aberration relating to virtual images of the observation optical system 10B of Example 2 illustrated in FIG. 2A.

Example 3

Optical data of the observation optical system of Example 3 are listed below.
magnification: 5.3 (times)
diopter: −1.0 (Dpt)
object distance: 389.9 (mm)
visual field range: φ65 (mm)
Data of the lens surface or the like of the observation optical system m of Example 3 are listed below in table 4.

TABLE 4

| Surf. N | R (mm) | D (mm) | n | vd |
| --- | --- | --- | --- | --- |
| 1 | 23.679 | 0.78 | 1.85026 | 32.27 |
| 2 | 13.8393 | 3.7 | 1.65844 | 50.85 |
| 3 | −1680 | 15.77 | | |
| 4 | INF | 30.57 | 1.75520 | 27.53 |
| 5 | INF | 0.52 | | |
| 6 | INF | 16.18 | 1.75520 | 27.53 |
| 7 | INF | 6.5 | | |
| 8 | −27.706 | 2.45 | 1.90366 | 31.32 |
| 9 | −7.882 | 1.97 | | |
| 10 | −5.482 | 0.58 | 1.75211 | 25.05 |
| 11 | 47.096 | 0.96 | | |
| 12 | 405 | 4 | 1.80420 | 46.5 |
| 13 | −10.019 | 0.2 | | |
| 14* | 22.874 | 3.5 | 1.62263 | 58.164 |
| 15* | −21.26 | 0.87 | | |
| 16 | INF | 2 | 1.51680 | 64.20 |
| 17 | INF | 11.5 | | |
| 18 (EP) | INF | | | |

Aspherical coefficients of the observation optical system of Example 2 are listed in table 5 below.

TABLE 5

Fourteenth Surface

K = −5.00, A4 = −3.300E−05, A6 = −6.887E−07, A8 = 4.256E−08,
A10 = −2.862E−10

Fifteenth Surface

K = 2.46, A4 = −5.112E−05, A6 = 8.161E−07, A8 = 9.092E−09,
A10 = 5.489E−11

Figure 3A:
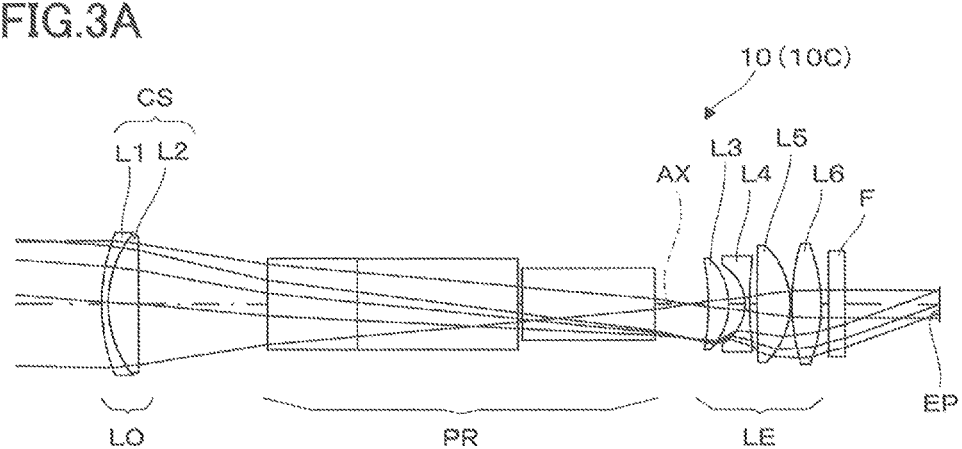
FIG. 3A is a cross-sectional view illustrating an observation optical system of Example 3.

FIG. 3A is a cross-sectional view of the observation optical system 10C of Example 3. The observation optical system 10C has the objective system LO, the reverse-erecting system PR, and the eyepiece system LE. The objective system LO has the first lens L1 having a negative power and the second lens L2 having a positive power. The lenses L1 and L2 are joined to each other. The eyepiece system LE has the third lens L3 having a positive power and having a concave surface at the object side, the fourth lens L4 having a negative power and having a concave surface at the object side, the fifth lens L5 having a positive power, and the sixth lens L6 having a positive power. As for the lenses, the first lens L1 is located at the object side and the sixth lens L6 is located at the pupil EP side. The first to sixth lenses L1 to L6 are made of glass. The lens surfaces at the object side and the pupil EP side of the sixth lens L6 are aspherical.

Figure 3B:
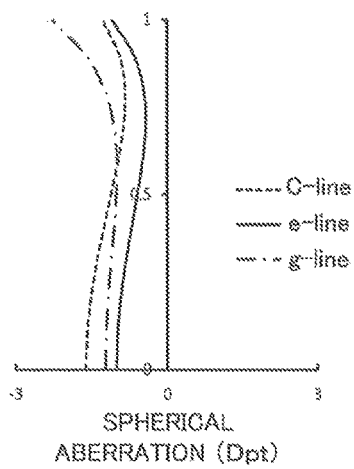
FIGS. 3B to 3D illustrate aberration charts of the observation optical system of FIG. 3A.
Figure 3C:
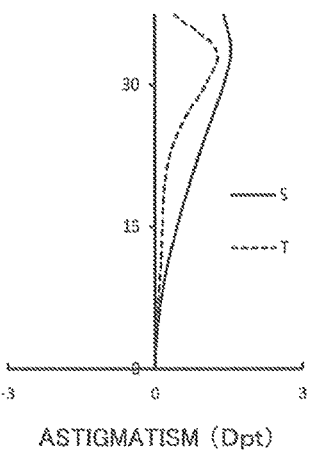
Figure 3D:
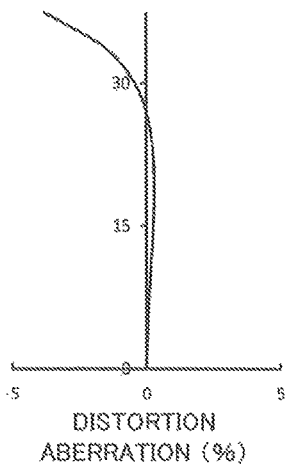

FIGS. 3B to 3D respectively illustrate spherical aberration, astigmatism, and distortion aberration relating to virtual images of the observation optical system 10C of Example 3 illustrated in FIG. 3A.

Although observation optical systems according to one or more embodiments have been described above, the observation optical systems according to the present invention are not limited to those described above. For example, one or more of the aforementioned embodiments may have a cover member having light permeability provided outside of the lens located closest to the object side and the lens located closest to the pupil EP side of the observation optical system 10, in consideration of scratch resistance, chemical resistance, and the like.

Although the first to sixth lenses L1 to L6 are made of glass in the aforementioned examples, the lenses other than the ones located closest to the object side and closest to the image side may be made of resin. Using a lens made of resin allows reduction in weight and cost.

A lens having substantially no power may be provided at a preceding or subsequent stage of the objective system LO, at a preceding or subsequent stage of the eyepiece system LE, or within the objective system LO or the eyepiece system LE.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. An observation optical system of a real-image type, comprising, in order from an object side:
    an objective system;
    a reverse-erecting system that erects an inverted image formed by the objective system; and
    an eyepiece system that allows a pupil to observe an erect image formed by the reverse-erecting system,
    wherein the objective system has exactly two lenses, a first lens having a negative refractive power and a second lens having a positive refractive power, disposed in that order from the object side,
    wherein the eyepiece system comprises, in order from the object side, a third lens having a positive refractive power, a fourth lens having a negative refractive power, a fifth lens having a positive refractive power, and a sixth lens having a positive refractive power, and
    wherein each of the third and fourth lenses adjacent to each other in the eyepiece system has a concave surface at the object side.

2. The observation optical system according to claim 1, wherein the objective system is a cemented lens having the first lens and the second lens joined together.

3. The observation optical system according to claim 1, wherein the eyepiece system has a lens at least one side of which is aspherical.

4. The observation optical system according to claim 1, wherein the observation optical system further comprises a parallel flat plate disposed between the eyepiece system and the pupil, the parallel flat plate comprising two flat surfaces parallel to one another.

* * * * *